United States Patent [19]

Smilansky et al.

[11] Patent Number: 5,495,535
[45] Date of Patent: Feb. 27, 1996

[54] METHOD OF INSPECTING ARTICLES

[75] Inventors: Zeev Smilansky, Kfar Meishar; Moshe Nissim, Raanana; Eyal Harel, Tel Aviv, all of Israel

[73] Assignees: Orbotech Ltd, Yavne, Israel; Orbotech Inc., Billerica, Mass.

[21] Appl. No.: 122,507

[22] PCT Filed: Jan. 28, 1993

[86] PCT No.: PCT/US93/00791

§ 371 Date: Sep. 24, 1993

§ 102(e) Date: Sep. 24, 1993

[30] Foreign Application Priority Data

Jan. 31, 1992 [IL] Israel ......................... 100824

[51] Int. Cl.⁶ ..................................................... G06K 9/00
[52] U.S. Cl. ........................ 382/145; 382/151; 382/294
[58] Field of Search .................................... 382/8, 44, 45, 382/46, 41, 141, 144, 145, 147, 151, 293, 294, 295, 296, 298; 348/95

[56] References Cited

U.S. PATENT DOCUMENTS

| | | | |
|---|---|---|---|
| 3,898,617 | 8/1975 | Kashioka et al. | 340/146.3 |
| 3,905,045 | 9/1975 | Nickel | 282/41 |
| 4,213,117 | 7/1980 | Kenbo et al. | 340/146.3 |
| 4,233,625 | 11/1980 | Altman | 358/101 |
| 4,238,780 | 12/1980 | Doemans | 340/146.3 |
| 4,247,203 | 1/1981 | Levy et al. | 356/398 |
| 4,325,077 | 4/1982 | Dunham | 358/101 |
| 4,334,241 | 6/1982 | Kashioka et al. | 358/107 |
| 4,435,835 | 3/1984 | Sakow et al. | 382/8 |
| 4,550,374 | 10/1985 | Meshman et al. | 358/101 |
| 4,590,607 | 5/1986 | Kauth | 382/44 |
| 4,630,225 | 12/1986 | Hisano | 382/8 |
| 4,635,293 | 1/1987 | Watanabe | 382/44 |
| 4,668,982 | 5/1987 | Tinnerino | 382/8 |
| 4,672,676 | 6/1987 | Linger | 382/8 |
| 4,680,627 | 7/1987 | Sase et al. | 382/8 |
| 4,720,635 | 1/1988 | Uga | 250/548 |
| 4,757,550 | 7/1988 | Uga | 382/8 |
| 4,758,782 | 7/1988 | Kobyashi | 358/105 |
| 4,783,826 | 11/1988 | Koso | 382/8 |
| 4,805,123 | 2/1989 | Specht et al. | 382/8 |
| 4,926,489 | 5/1990 | Danielson et al. | 382/8 |
| 4,953,100 | 8/1990 | Yotsuya | 382/8 |
| 4,972,311 | 11/1990 | Holdgrafer et al. | 382/8 |
| 4,989,082 | 1/1991 | Hopkins | 358/101 |
| 5,023,917 | 6/1991 | Bose et al. | 382/8 |
| 5,048,094 | 9/1991 | Aoyama et al. | 382/8 |
| 5,129,014 | 7/1992 | Bloomberg | 382/8 |
| 5,134,664 | 7/1992 | Clough et al. | 382/8 |
| 5,206,917 | 4/1993 | Ueno et al. | 382/44 |

*Primary Examiner*—Joseph Mancuso
*Attorney, Agent, or Firm*—Benjamin J. Barish

[57] ABSTRACT

A method of inspecting an article with respect to a stored list of reference features by scanning the article to detect online features, transforming their coordinates according to registration transformation parameters to correct for misregistration of the article, and comparing the transformed coordinates of the online features with those of the stored reference features for matches. According to this method, an initial estimate of the required registration transformation parameters is provided and is dynamically improved by continuously computing and periodically updating the estimate from the coordinates of the online features detected during the scanning of the article and the coordinates of the stored reference features.

16 Claims, 16 Drawing Sheets

FIG. 8 (BOOTSTRAP PROCEDURE)

METHOD OF INSPECTING ARTICLES

FIELD AND BACKGROUND OF THE INVENTION

The present invention relates to a method of inspecting articles for defects and the like. The invention is particularly useful in automatic optical inspection systems for printed circuit boards (PCBs), and is therefore described below with respect to this application.

Printed circuit boards are often optically inspected with respect to a reference, namely a flawless or almost flawless board. Such a reference is characterized by a list of features created either by processing a board known to be substantially flawless, or by processing computer aided manufacturing (CAM) data of such a board. The list of features may include any number of features, typically from a few thousand to tens of thousands. Each feature is identified by its coordinates (x,y), and by a code indicating the feature type and enabling the indexing of as many different types of features as necessary for any given PCB.

To find defects in a PCB that is to be inspected, a list of features characterizing the inspected PCB (commonly called an online list) is prepared and is then compared with a reference list of the features previously prepared and stored for comparison purposes. In order to produce the online list, the PCB is optically scanned, and its image is processed to detect the features therein. Any feature appearing in the online list with no match in the reference list is termed an "excess feature" and is reported as a defect. Similarly, any feature appearing in the reference list with no match in the online list is termed a "missing feature" and is also reported as a defect.

When the online list and the reference list are in perfect geometrical registration, the matching is quite simple since it is only necessary to compare the two lists and to determine whether the feature type and coordinates of one match those of the other. In reality, the coordinates are never in perfect geometrical registation so that such a simple comparison procedure cannot be performed. Therefore, the coordinates are not required to be exactly the same, but they should be close enough, as specified by the user, to allow a discrepancy parameter, termed "reference tolerance", to be used in the matching. The reference tolerance is typically considerably smaller than the design grid of the PCB. If it is smaller than the manufacturing process precision or the feature-detector precision of the optical inspection system, the false alarm rate of the inspection will increase.

It will thus be appreciated that the comparison of the inspected article (sample) with the reference is greatly facilitated by having the sample placed on the scanner with as perfect registration as possible to the reference. Also important is the geometrical accuracy of the inspection system itself.

Various mechanical, optical or electronic aids are presently used for registering PCBs in order to permit their optical inspection with respect to a reference list of features.

Mechanical aids usually take the form of registration pins, sideboards, and the like; see for example U.S. Pat. Nos. 4,783,826 and 4,799,175. Using such mechanical means requires special and different preparations for different types of PCBs. For example, using registration pins requires constructing the pins on the scanner table, punching holes in the articles to be inspected, and manual or other mechanical alignment of the holes with the registration pins. Such mechanical aids thus involve significant additional costs and time for this extra mechanical handling.

Computational registration is often achieved by having easily detected fiducial marks in perfect registration with the PCB pattern; see for example European Patent Application 0206712. This method requires an extra scan for the fiducials prior to inspection, and therefore significantly increases the overall inspection time. Only after the fiducials have been scanned can the misregistration be calculated and fixed. Also, the fiducial marks require allocations of extra space on the PCBs in addition to the functional PCB pattern.

Some systems, for example as disclosed in U.S. Pat. No. 4,805,123, carry out local registration by pixel-wise correlating reference image to online image. This requires the reference images to be stored, instead of just the characteristic features. Because of the extreme computational complexity of carrying out correlations between images, such a system can only compensate for smaller amounts of misregistration and can be implemented, as a practical matter, only on special-purpose hardware.

Still other systems, such as described in European Patent Application 0247308, employ dynamic distortion control to compensate for local distortions, rather than for global misregistration. Such systems, therefore, still require preliminary registration, for example according to one of the above-described techniques.

OBJECTS AND BRIEF SUMMARY OF THE INVENTION

An object of the present invention is to provide a method having advantages in the above respects for inspecting an article with respect to a stored list of reference features.

More particularly, an object of the present invention is to provide a method of inspecting an article with respect to a stored list of reference features which obviates the need for pre-registering the inspected article, mechanically, optically, or computationally, without requiring extra hardware and with little extra computational load, and which in addition compensates for various kinds of scanner geometrical distortions and production errors of scaling in the article.

According to the present invention, there is provided a method of inspecting an article with respect to a list of reference features each identified by its coordinate location, comprising scanning the article to generate online data, identifying detected features and their coordinates detected during the scanning of the article; transforming the coordinates of the detected features according to registration transformation parameters to correct for global misregistration of the article; and comparing the transformed coordinates of the online features with those of the reference features for matches. The registration parameters of the overall article are determined by scanning an initial area of the article; generating for the initial area, a list of the defined features with their coordinates; pairwise matching the detected features and their coordinates with the reference features and their coordinates for the initial area; computing an initial estimate of optimal registration transformation parameters required to minimize disparities between the pairwise matched detected and reference features in the initial area according to a misregistration transformation model; and dynamically improving the initial estimate of the optimal transformation parameters by progressively increasing the scanned area of the article and progressively updating the initial estimate of the optimal transformation parameters according to the misregistration transformation model to provide optimal registration for the detected and reference features with respect to the complete area scanned.

The "misregistration" of the article to be corrected includes any disparity between the reference feature locations and the scanned feature locations, whether the disparity is introduced by article placement, scanner errors, or production scaling errors.

According to still further features in the described preferred embodiment, computing the initial estimate of the required registration transformation parameters includes: determining, for each detected online feature in the initial area, all the reference features of the same type and with a maximal misregistration distance from the detected online feature; identifying such online and reference features as matching pairs; and utilizing the matching pairs for computing the initial estimate of the required registration transformation parameters.

According to still further features in the described preferred embodiment, the initial estimate of the required transformation parameters is periodically updated by: providing a plurality of registers for accumulating the coordinates of the online and reference features; incrementing the registers for the respective coordinates for each matching pair; and utilizing the current values of the registers for updating the transformation parameters.

As will be described more particularly below, such a method, in which the coordinates of the detected features are transformed by dynamically changing parameters, eliminates the need for mechanical aids, such as registration pins, and also the need for an extra scan of the article when the registration is effected by fiducial marks. A particularly important advantage of the novel method of the present invention is that it requires very little extra, in terms of time as well as resources, over the standard method of feature matching as in the prior art. The method of the present invention also requires substantially simpler computations, as compared to the prior systems based on pixel-wise correlating reference image to online image, and can be implemented by software included in general purpose computers.

The inspection system is particularly advantageous in the otherwise difficult situations where the actual misregistration distance is larger than the distance between features, or where the features have a repeating pattern of a period smaller than the misregistration distance.

Another important advantage is that the system does not rely on the existence of fiducials or other landmarks in the article.

The misregistration data outputted by the novel system may also be utilized for finding defects in various other types of inspection systems where good registration is needed.

Further features and advantages of the invention will be apparent from the description below.

BRIEF DESCRIPTION OF THE DRAWINGS

The invention is herein described, by way of example only, with reference to the accompanying drawings, wherein:

FIG. 5 illustrates a list of features arranged according to a lexicographical ordering;

DESCRIPTION OF A PREFERRED EMBODIMENT

Overall System

Figure 1:
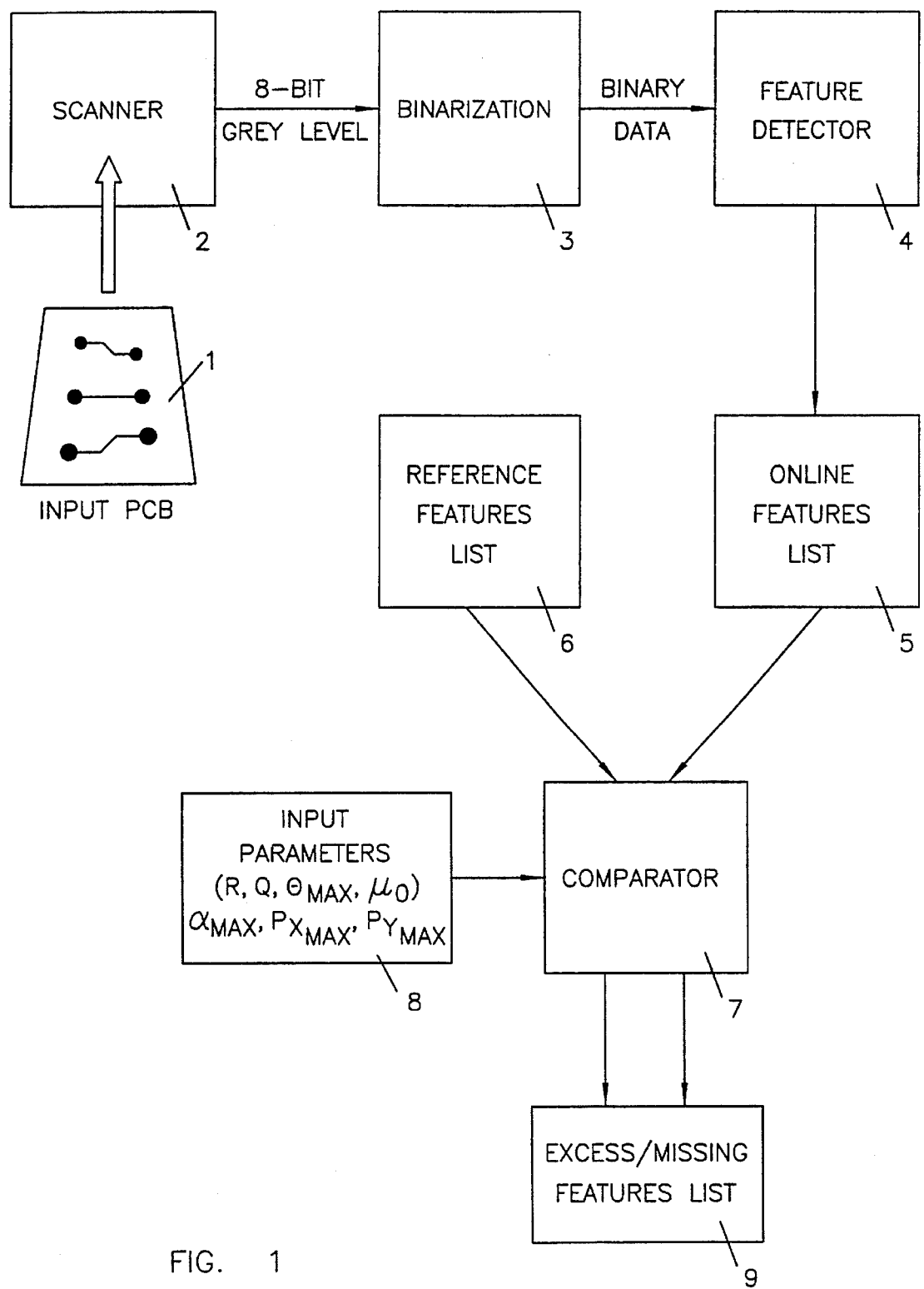
FIG. 1 is a block diagram illustrating an overall automatic optical inspection system constructed in accordance with the present invention for optically inspecting PCBs.

FIG. 1 is a block diagram illustrating the various units of an automatic optical inspection system for optically inspecting printed circuit boards.

Thus, the PCB (printed circuit board) 1 is first scanned by a scanner unit 2, which outputs 8-bit gray level data which, after being converted by binarizator 3 to binary data (black, white), is fed to a feature detector unit 4. Unit 4 detects the various features of the inspected PCB and identifies each feature by its type (e.g., junctions, pads, open ends, pinholes, islands, etc.) and by its coordinates. This data is stored in the form of an online features list 5.

The online features list from memory unit 5, and the reference features list previously stored in memory 6, are inputted into a comparator 7 which compares the two lists of features for excess features and missing features in the light of prespecified parameters defining the misregistration bounds inputted into the comparator 7 via an input unit 8. The prespecified input parameters include the values of Q, R, $\sigma_{max}$, $\alpha_{max}$, $P_{Xmax}$, $P_{Ymax}$ and $\mu_o$, where: Q is the reference tolerance; R is the maximal assumed misregistration radius, which is an upper bound on the distance between any point in the scanned area of the PCB and its position in the reference coordinate system; $\sigma_{max}$ is a maximal assumed misregistration angle between the inspected PCB and the reference; $\alpha_{max}$ is the maximal assumed angular deviation between the light sensor array and the Y-motion; $P_{Xmax}$ and $P_{Ymax}$ are the maximal assumed scaling errors; and $\mu_o$ is the position error. These misregistration bounds depend on the quality of the preliminary alignment between the loaded PCB and the reference, on the scanner precision, and on the precision of the production and measuring tools.

Comparator 7 outputs to a memory 9 a list of excess features, namely features present in the online list but not in the reference list, and also missing features, namely features in the reference list but not in the online list.

Figure 2:
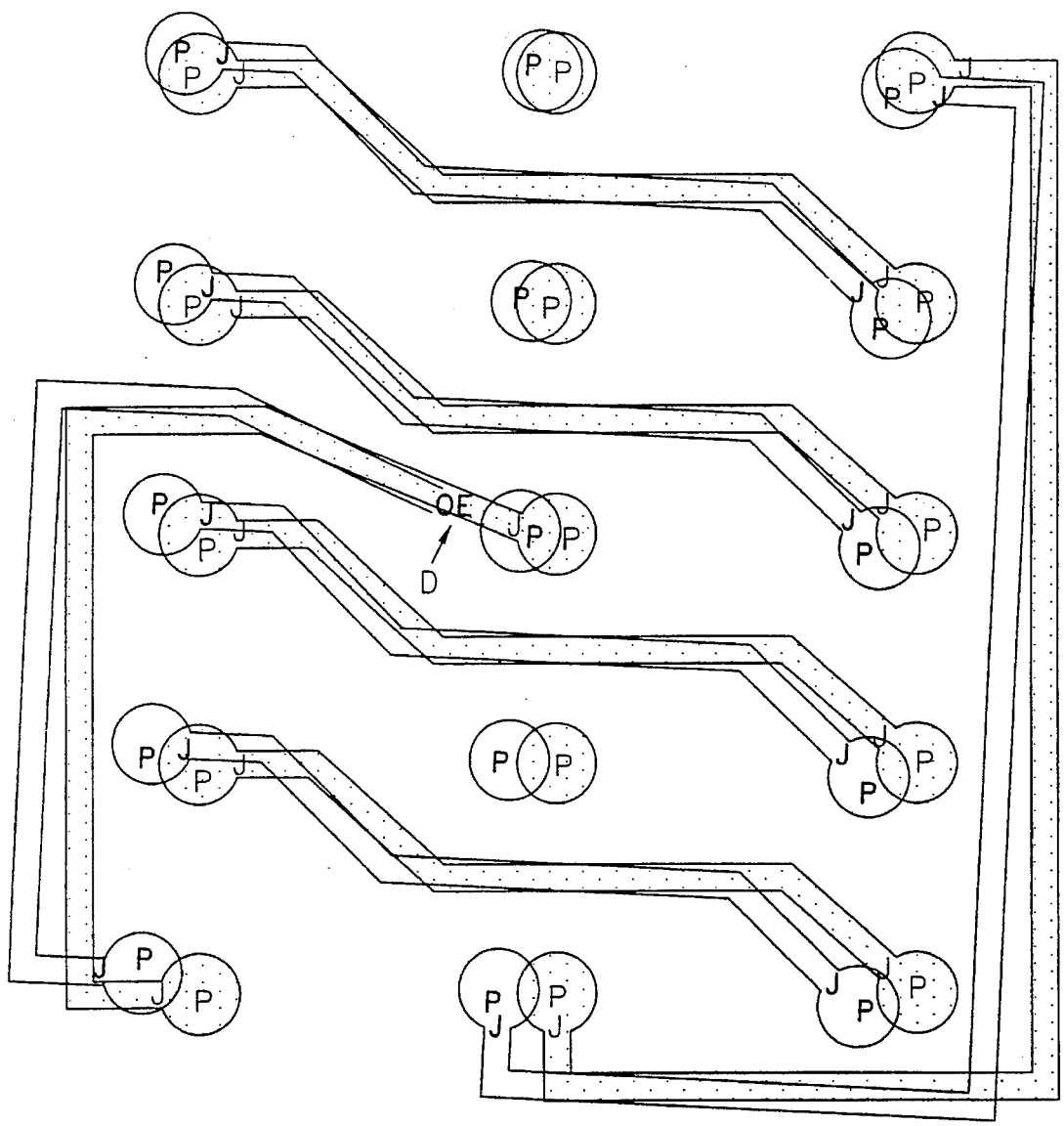
FIG. 2 illustrates an inspected PCB with some features marked on it.
Figure 3:
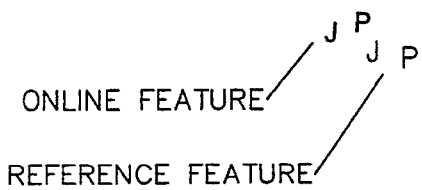
FIG. 3 graphically illustrates inspected board features of FIG. 2 as imperfectly registered with respect to corresponding reference features.

FIG. 2 illustrates the image of a PCB being inspected having two types of features: pads (P) and junctions (J), with a defect D in the form of an open end (OE) at the central pad (P). FIG. 3 is a graphical illustration of the two features lists: the lighter-intensity letters "P" and "J" are the reference features, and the heavier-intensity letters are the online features of the inspected PCB. It will be seen that the online feature list also shows the defect D to be an open end (OE) which is seen as an excess feature present in the online but not in the reference.

Figure 4:
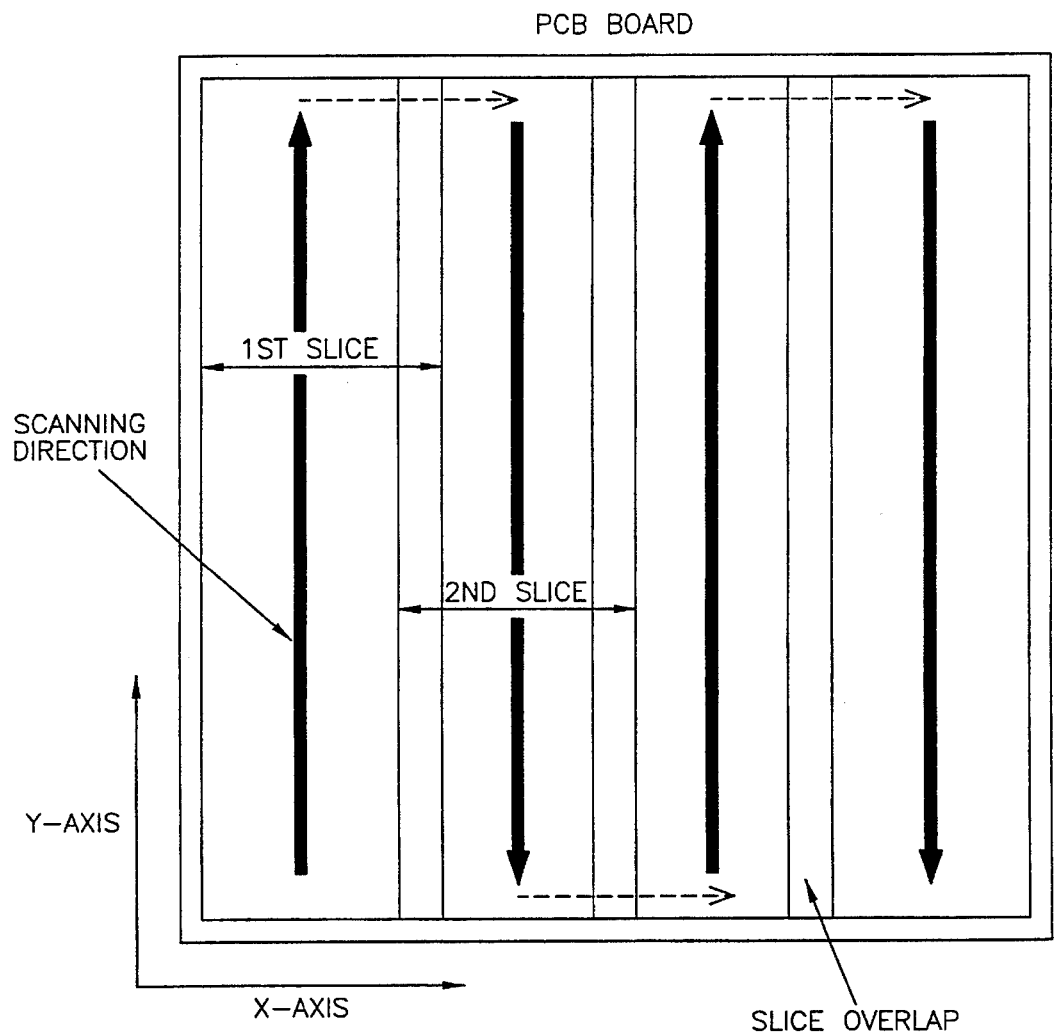
FIGS. 4, 4a and 4b illustrate the manner of scanning a PCB when optically inspecting it.
Figure 4A:
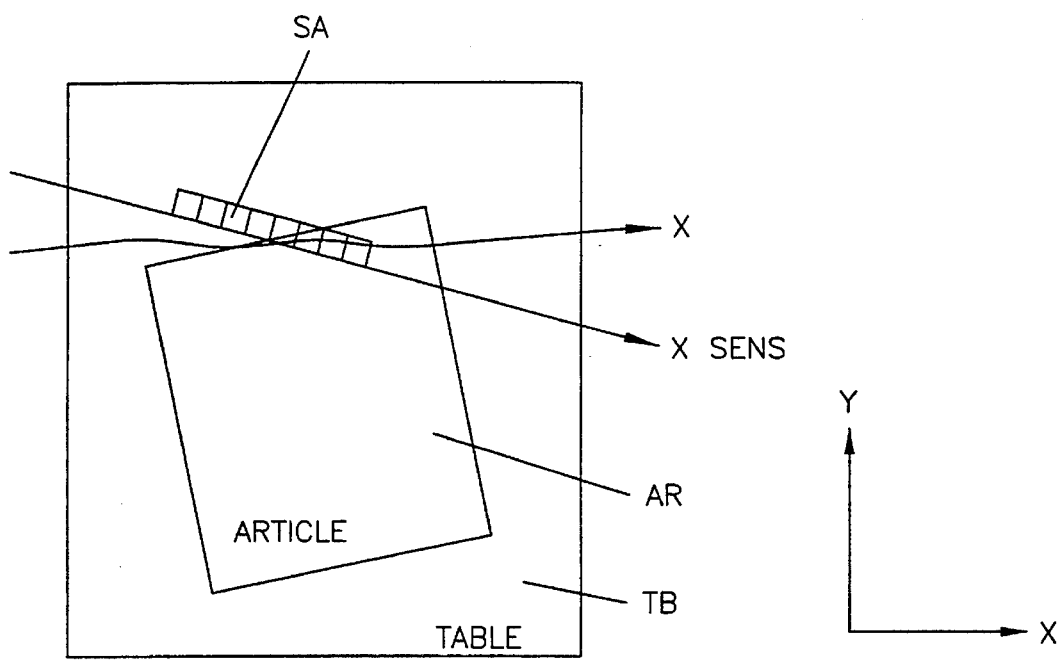
Figure 4B:
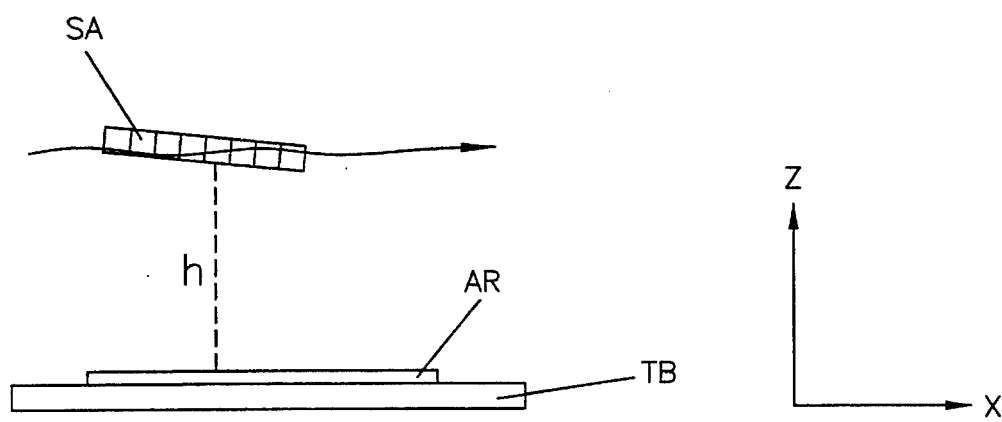

The scanning of the PCB is performed in a plurality of slices, as shown in FIG. 4, with each slice partially overlapping the preceding slice. The overlap is provided to assure that a complete feature is detected. Each slice is scanned by moving the table TB (FIGS. 4a, 4b) on which the article AR is mounted in the Y-direction. A linear array of light sensors SA is positioned perpendicularly to the direction of motion. Between the slices, the optical apparatus is moved in the X-direction (to the right). The first few features are localized in the beginning of the first slice. Consecutive features may be expected to lie relatively near each other, at least in their Y-coordinates, as the temporal arrival order of the features parallels their geometric order. Preliminary misalignment may be in the order of 0.5–2.0 mm, and could even be much larger.

As an example, a segment of a feature list is illustrated in FIG. 5. It can be seen that the list begins with the first Y-coordinate 2000, which corresponds to two features with X-coordinates 12634 and 12644. The types of these features (marked by T) are identical. This means that two features of the same type are located on the same line.

As mentioned above, the comparison in comparator 7 (FIG. 1) compares both types and geometric positions (x,y coordinates). Many algorithms are known in the prior art for comparing feature types according to the particular application, and therefore no specific type-matching algorithm is described herein.

Figure 6:
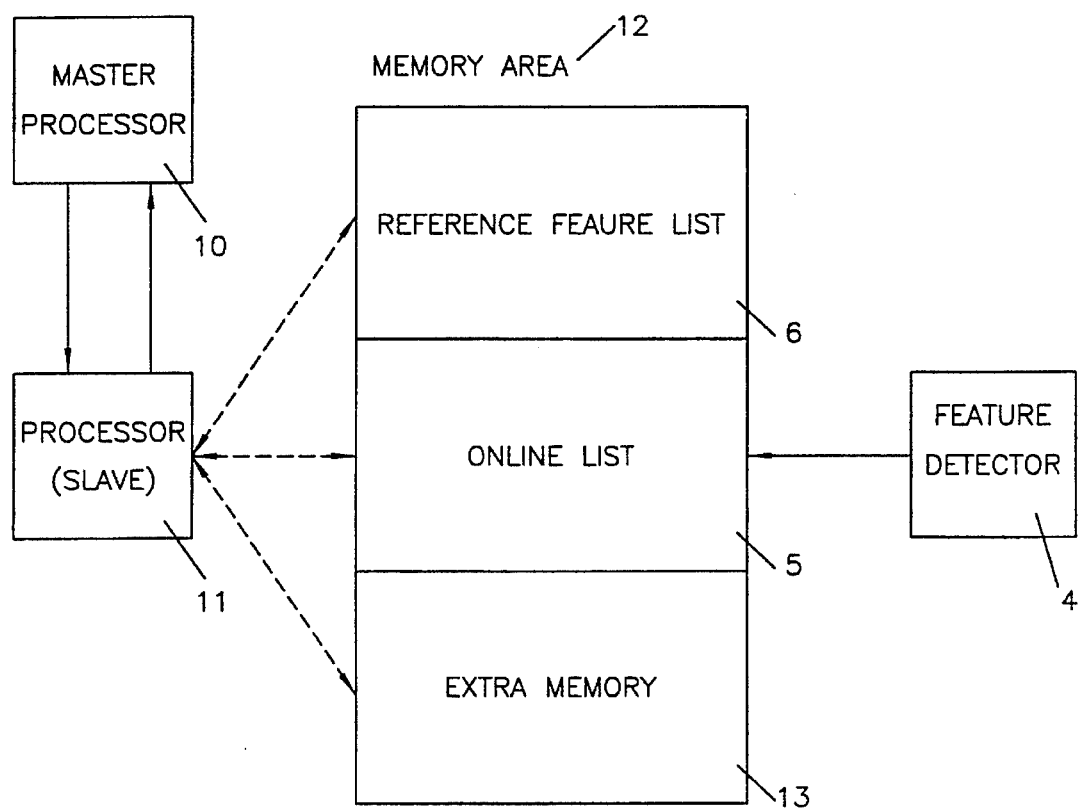
FIG. 6 is a block diagram illustrating the hardware in the comparator unit in the optical inspection system of FIG. 1.

FIG. 6 schematically illustrates the inspection apparatus as including a master processor 10 for controlling the scanning operation, including image processing, feature detection and feature comparison as illustrated in FIG. 1. The system further includes another processor 11 which acts as a slave to carry out the tasks of comparing the reference feature lists and the online feature lists, and of dynamically registering them. The slave processor 11 includes a memory area 12 which is programmed according to the software required for comparing the reference and detected feature lists and dynamically registering them. The memory area 12 of the slave processor 11 includes memory area 5 (FIG. 1) for storing the reference feature list, memory area 6 for storing the detected feature list, and extra memory area, indicated at 13, for storing the program, buffers, registers, etc., to enable the system to carry out the task of comparing the reference and online features lists and dynamically registering them. The size of the memory 12 in the slave processor 11 is therefore proportional to the expected number of features in a single PCB. As one example, the slave processor 11 may be an Intel 80386 digital processor having a memory of 1 Mb, enabling it to handle approximately 50K features.

As described earlier, at some time before the inspection a reference list is created from a flawless sample according to the type of PCB to be inspected. Prior to the initiation of an inspection scan, the memory area 12 in the slave processor 11 (which serves the comparator unit 7 in FIG. 1), is loaded with the necessary software, the reference list, and also the input parameters (Q, R, $\sigma_{max}$ and $\mu$, FIG. 1) which define the misregistration bounds and which depend on the quality of the preliminary alignment between the loaded PCB and the reference.

The system may then be used for scanning the PCB to generate the online feature list, which is compared with the stored reference feature list to locate defects (excess features or missing features), as indicated by box 9 in FIG. 1.

As will be described more particularly below, the method involves two stages: (1) a preliminary registration stage, in which a "bootstrap procedure" is performed to compute an initial estimate of the relative coincidence of the two lists and the transformation to be applied on the online list bringing it to the reference coordinate system; and (2) a main matching stage, involving two tasks ("processes"), namely: (a) comparing the two lists after introducing the initial estimate of the transformation parameters; and (b) dynamically improving the transformation parameters as the online data arrives from the continuation of the scanning of the PCB after the initial area.

Figure 7:
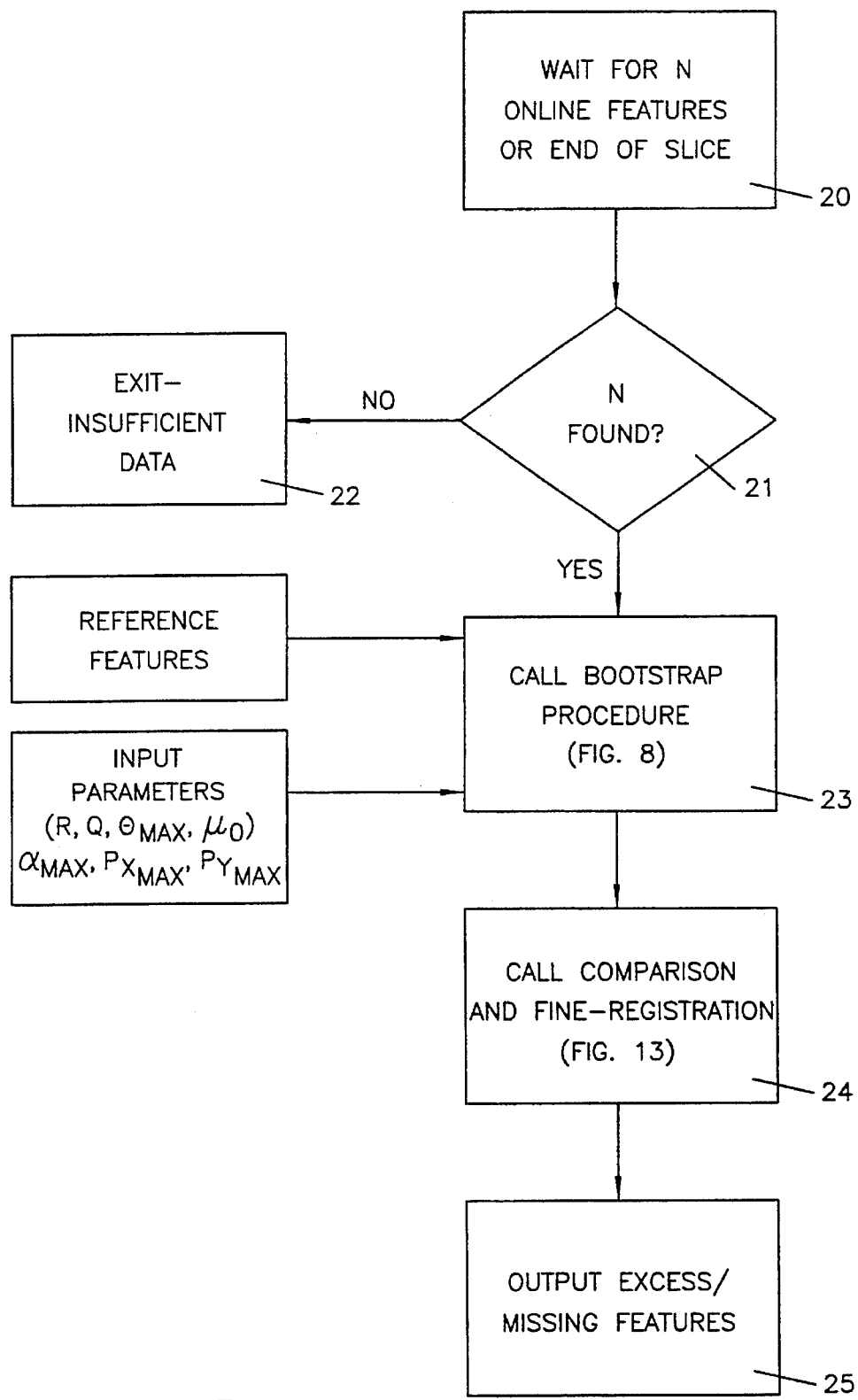
FIG. 7 is a flow diagram illustrating the overall inspection method.

FIG. 7 more particularly illustrates the comparator flow chart. Thus, the system first scans an initial area of the PCB until "N" (e.g., 128) online features have been detected, or the end of a slice has been reached (box 20). If in scanning the initial area the predetermined number (N) of online features has not been detected (box 21), the inspection process is terminated since there is insufficient data (box 22).

If N online features have been detected, the first stage, namely the bootstrap procedure stage is called (box 23). In this stage, an initial estimate of the registration transformation parameters is computed based on the relation of the detected online feature coordinates with respect to the reference feature coordinates. The bootstrap procedure indicated by block 23 in FIG. 7 is more particularly illustrated in FIGS. 8–12 to be described below.

After the initial estimate of registration transformation parameters has been computed, the system continues to scan further areas of the PCB to detect further online features and their coordinates, and utilizes their relation with the reference feature coordinates for updating the estimate of the registration transformation parameters. The updated parameters are then utilized in a fine-registration procedure (more particularly shown in FIG. 13) to transform the coordinates of the further online features (box 24). The system finally outputs a list of the defects, i.e., excess features and missing features (box 25).

To carry out the above computations, a mathematical model of the misregistration transformation is built. This allows devising an efficient algorithm for computing the model parameters, given the inspection data, and also controlling corection transformations introduced into the system (which are restricted to the allowed model), thus preventing defect misdetection.

The misregistration transformation model is characterized by the article production and mounting errors and by the scanner repeatable geometrical distortion which affect the geometrical system produced by the scanner, including the following kinds of flaws/misalignments:

(a) the angular deviation ($\alpha$) caused by the lightsensor array not being exactly perpendicular to the Y-direction motion;

(b) misregistration angle ($\theta$) caused by the article not being exactly parallel to the reference because of the mounting misregistration, and/or the angular discrepancy between the table and motion direction (scanner distortion);

(c) scaling errors in both directions ($P_x$ and $P_y$) because of the article production and/or scanner problems; and (d) optical distortions along the sensor axis, especially variations in magnification (because of varying distance h (FIG. 4b) between the sensors and the article surface).

The Bootstrap Procedure

Figure 8:
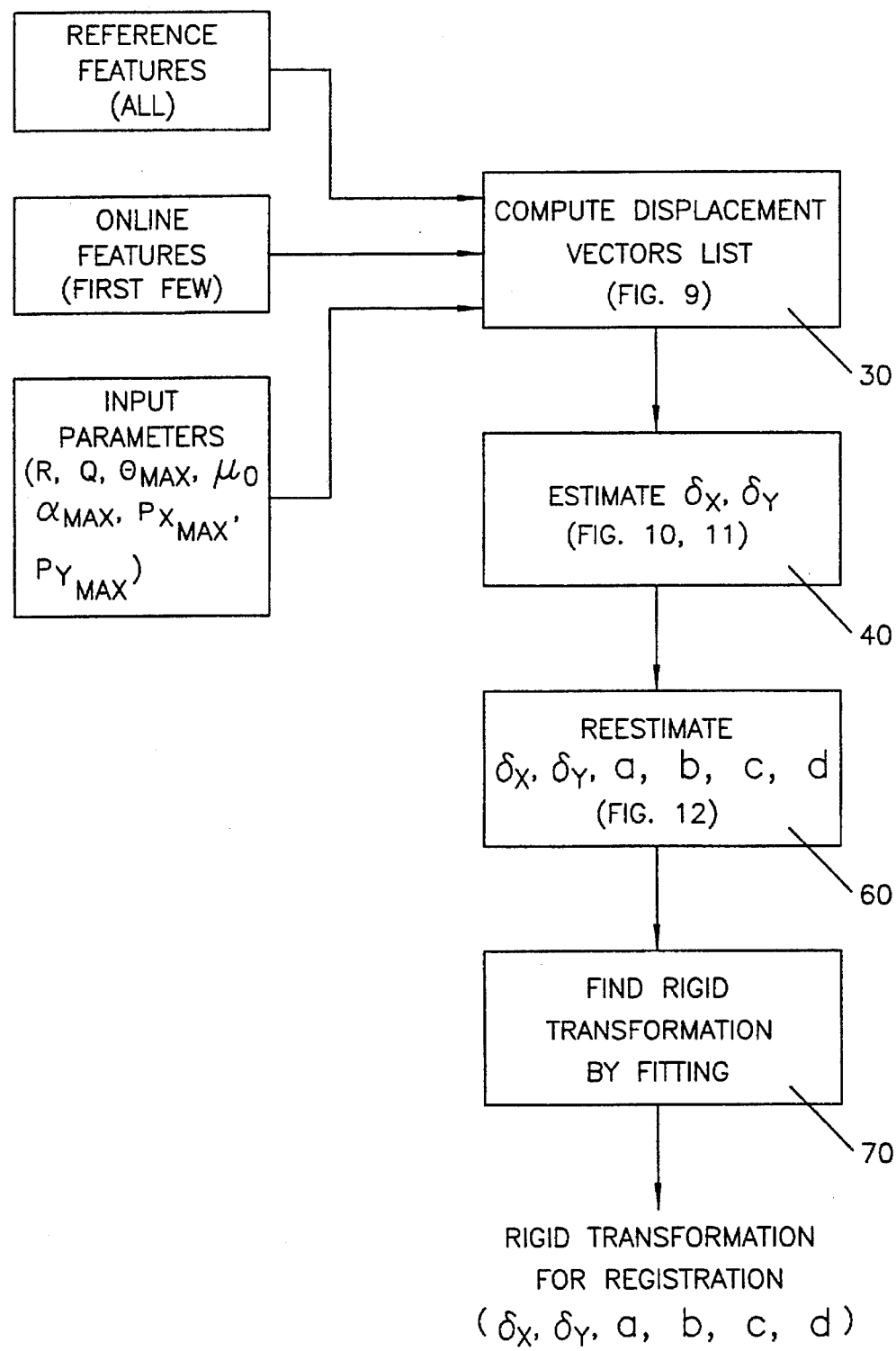
FIG. 8 is a flow chart illustrating the bootstrap operation for producing the initial and updated estimates of the transformation parameters.

FIG. 8 is a flow chart illustrating the bootstrap procedure represented by box 23 in FIG. 7, and FIGS. 9–12 are flow charts illustrating more particularly some of the operations involved in the bootstrap procedure of FIG. 8.

It can be shown that for a single slice said distortion effects (except optical distortion of a scanner) can be modeled as an affine transformation utilizing six variables:

$a$, $b$, $c$, $d$, $\delta x$ and $\delta y$:

$$x^r = ax + by + \delta x,$$
$$y^r = cx + dy + \delta y$$

Eq. 1 where $\delta x$, $\delta y$ are translational parts of misregistation correction transformation parameters; a, b, c, d are multiplicative parts of misregistration correction transformation parameters; x, y are the coordinates before registration, and $x^r$ and $y^r$ are the coordinates after registration (i.e., in the reference space).

The function of the bootstrap procedure is to produce a first, initial estimate of said misregistration correction transformation parameters, which will be continuously or periodically updated once the bootstrap procedure is completed and as more-online data becomes available.

In case where only article placement correction is required, the bootstrap procedure computes transformation parameters of the special, simpler form as follows:

$$a = \cos \theta, \ b = -\sin \theta, \ c = \sin \theta, \ d = \cos \theta$$

Eq.1a

In the more general case, connection between the model parameters a, b, c, d and the physical scanner distortion and article placement parameters $\theta$, $\alpha$, $S_x$, $S_y$ can be shown as follows:

$$a = S_x \cos \theta / \cos \alpha \qquad b = -S_x \sin \theta / \cos \alpha$$
$$c = S_y \sin(\theta - \alpha)/\cos \alpha \qquad d = S_y \cos(\theta - \alpha)/\cos \alpha$$

Eq. 1b

Different slices can be shown to differ only in their $\delta_x$ and $\delta_y$ but all have the same a, b, c and d parameters.

As shown by the flow chart in FIG. 8, the first step in the bootstrap procedure is to compute a displacement vectors list for each online feature (box 30). The flow chart of FIG. 9 more particularly shows how this is done.

Figure 9:
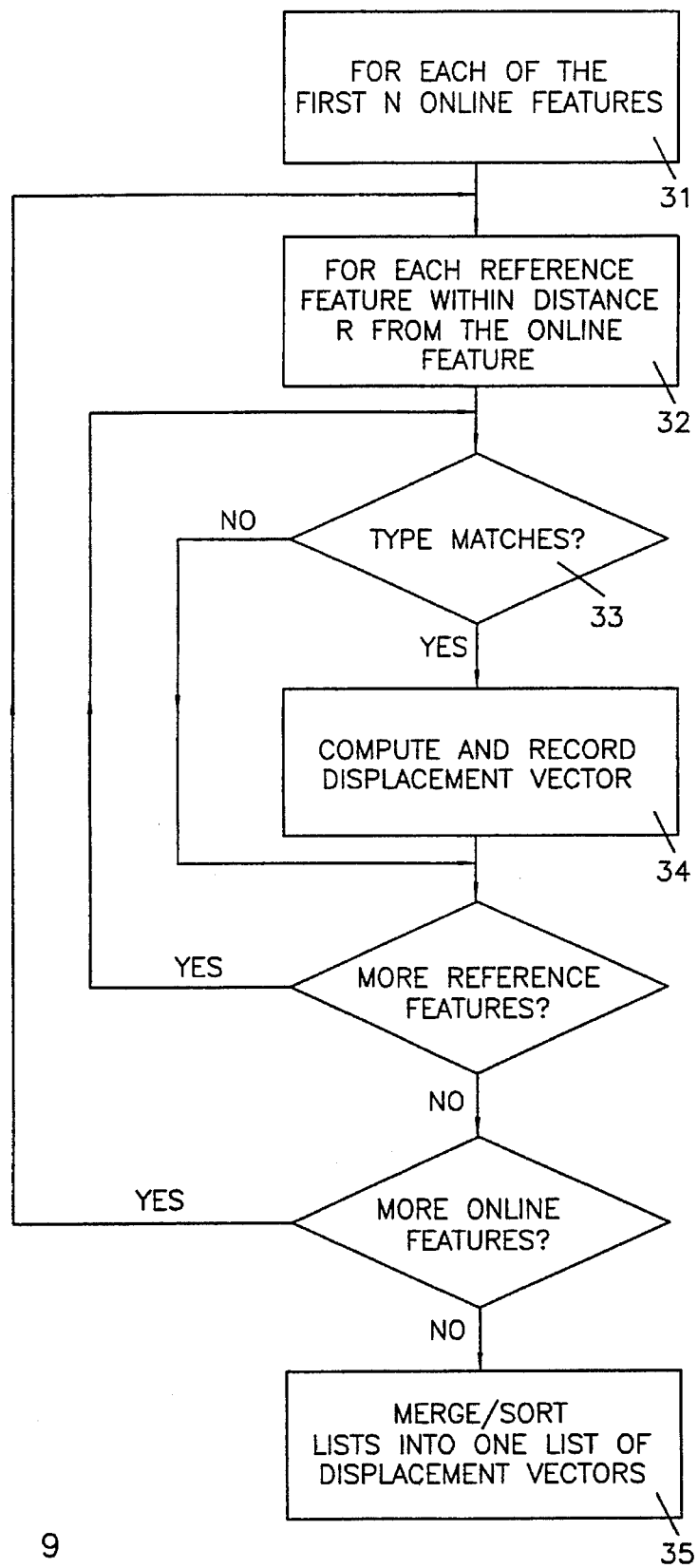
FIGS. 9–12 are flow charts illustrating in more detail certain steps in the bootstrap operation shown in the flow chart of FIG. 8.

Thus, as shown in the flow chart of FIG. 9, for each of the N online features (box 31), and for all the reference features within the misregistration radius R (box 32), determine whether a type match exists (box 33).

Next, in order to determine whether a match exists between an online feature with coordinates $(x_n, y_n)$ and type $T_n$, and a reference feature with coordinates $(x', y')$ and type T', the following must hold:

$$|x'-x_n| \leq R \text{ and } |y'-y_n| \leq R$$

Eq. 2 and type $T_n$ must match the type T'. The pair, of online feature with its matching reference feature, is called a matching pair.

Type matching procedures are well known in the prior art according to the particular application. The decision rules are usually derived heuristically, sometimes by the user. Since the novel system is not concerned with any particular type maching procedure, a particular type matching procedure is not described for the sake of conciseness.

The next step (box 34, FIG. 9) is to compute and record, for each maching pair found, the displacement vector, according to the following equation:

$$(\Delta_x, \Delta_y) = (x' - x_n, y' - y_n)$$

Eq. 3

The so-computed displacement vectors are used in producing a displacement vectors list of the N online features (box 35, FIG. 9).

The full reference list is ordered in increasing lexicographical order, primarily by y and secondarily by x, and therefore the n'th displacement-vectors list is similarly ordered by virture of being a sublist of the full reference list from which a constant vector $(x_n, y_n)$ has been subtracted. This greatly facilitates the task of producing one sorted list from the N displacement-vectors lists, by successively merge-sorting them (cf. The Art of Computer Programming D. H. Knuth, Reading, Mass. Addison-Wesley, 1968., vol, 1, section 2.3.3). Displacement vectors appearing in more than one list are found during the merges, and recorded only once, with a population count. The displacement-vectors lists of the online features are thus merged into one list of displacement vectors (box 35).

The next operation performed by the bootstrap procedure illustrated in the flow chart of FIG. 8 is to estimate the correction parameter $\delta_x$, $\delta_y$, as shown by block 40 in FIG. 8. This requires a correlation function, W( ), to be computed. The flow chart of FIG. 10 more particularly illustrates how this is done.

Figure 10:
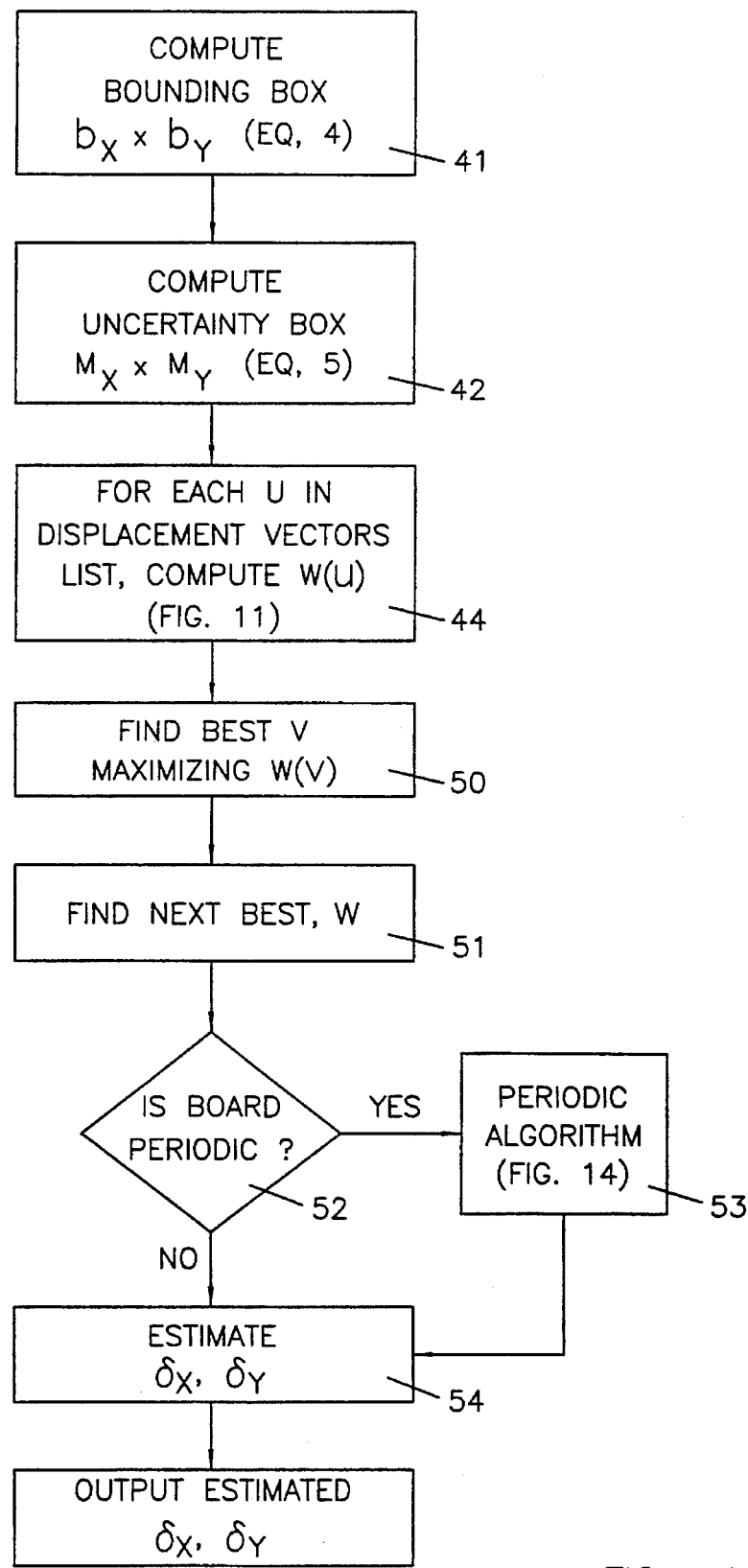

Thus, as indicated by box 41 in FIG. 10, the size of the scan zone of the first N online features is determined by computing the bounding-box of these features. The size of the bounding box is denoted by $b_x \times b_y$; that is:

$$b_x = \max x_n - \min x_n, \ b_y = \max y_n - \min y_n$$

Eq. 4

The amount of "allowable noise" in the correct displacement vector (the one best describing the misregistration in the initial scan zone) is then determined (box 42). This amount is defined separately in the two directions (x,y) and is termed the "uncertainty-box". Contributing to its size are two factors: The first factor (and usually the larger) is the angle ($\theta$) between the PCB and the reference, which appears as "noise" in this phase when using only displacement and not the angle. This factor is estimated by the size of the bounding-box and an upper bound on the angle (input parameter $\theta_{max}$).

The second factor encompasses all other noises in the reporting of the position of a feature, including image quantization (pixel size), feature-detection mechanism errors, scanner mechanics, scanner unmodeled geometrical distortion, etc. An upper bound on this factor is termed "position error" and is denoted by the input parameter "$\mu_o$". Finally, the uncertainty-box size, denoted by $M_x \times M_y$, is computed as follows:

$$M_x = b_y \theta_{max} + \mu_x, \ M_y = b_x \theta_{max} + \mu_y$$

Eq. 5

$$\mu_x = \mu_{ox} + (P_{Xmax}) \cdot b_x$$
$$\mu_y = \mu_{oy} + \alpha_{max} b_x + (P_{Ymax}) \cdot b_y$$

Eq. 5a

Where $P_{Xmax}$ ($P_{Ymax}$) is a maximal assumed difference between $P_x$ ($P_y$) and 1.

For each vector $u = (u_x, u_y)$ in the displacement-vectors list, we compute W(u), the correlation function applicable to our situation. The correlation function W(u) is the number of displacement-vectors $v = (v_x, v_y)$ which lie in the uncertainty-box centered around u, that is, which satisfy:

$$|v_x - u_x| \leq M_x/2, \text{ and } |v_y - u_y| \leq M_y/2,$$

Eq. 6 with population taken into account. This computation is relatively intensive, but the fact that the displacement-vectors list is sorted provides an efficient algorithm for computing the function W(u) (box 44).

The main loop is on u (a vector in the displacement-vectors list) in the order of the displacement-vectors list. Thus, successive u vectors come in increasing lexicographical order. For each u we shall compute W(u) (box 44). The manner of doing this is more particularly illustrated in the flow chart of FIG. 11.

Figure 11:
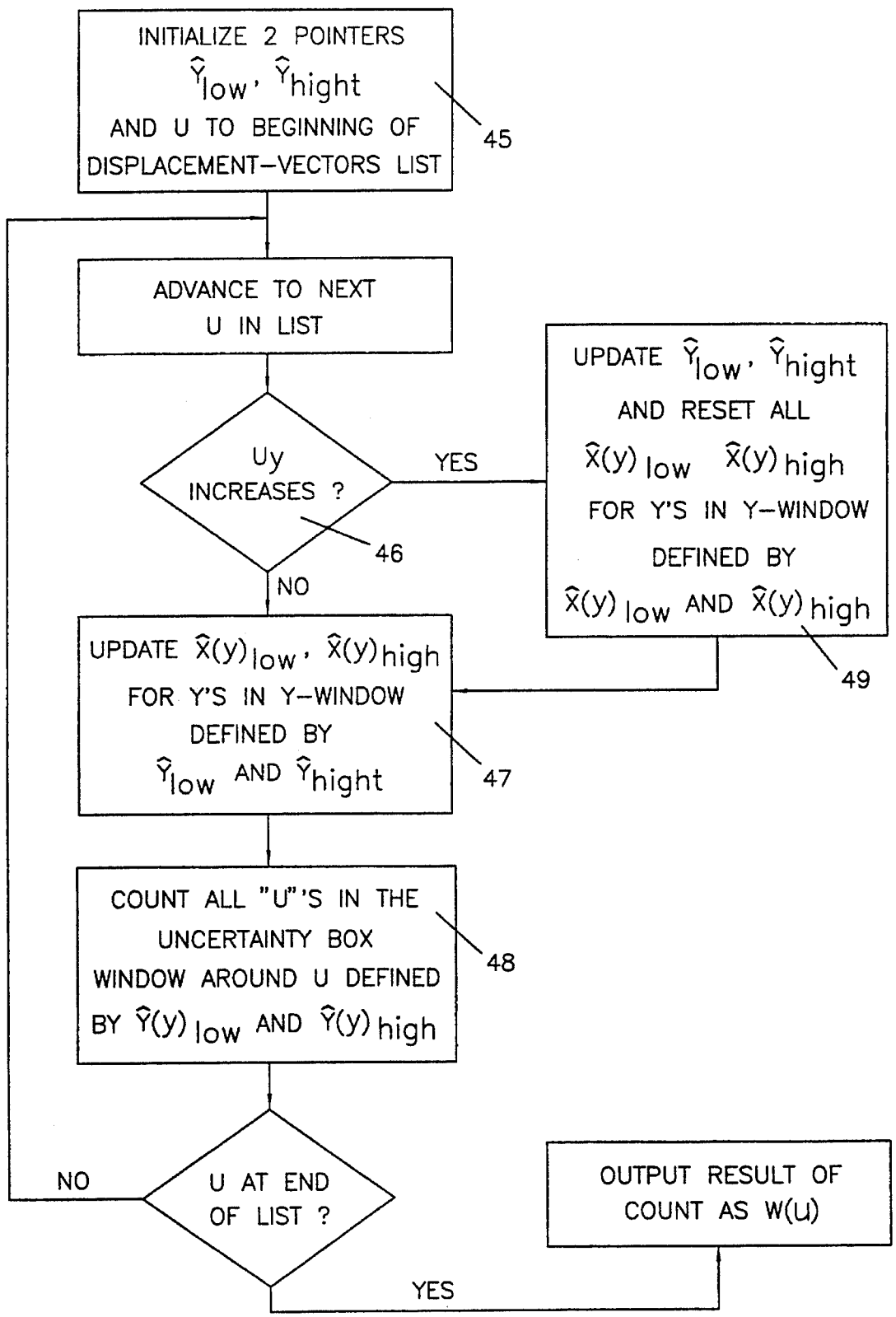

Thus, as shown by box 45 in FIG. 11, we first define two pointers, $\hat{Y}_{low}$ and $\hat{Y}_{high}$, in the displacement-vectors list.

Throughout the u-loop, $\hat{Y}_{low}$ points to an element of the displacment-vectors list whose y value is the smallest in the list which satisfies $y \geq u_y - M_y/2$; and $\hat{Y}_{high}$ points to an element of the list whose y value is the smallest in the list which satisfies $y > u_y + M_y/2$. These pointers need updating only when $u_y$ increases, that is, when proceeding to the next u in the u-loop (box 46) and $u_y$ changes.

The update is a simple matter of incrementing each pointer until it satisfies its "normal" condition again. u defines a set of vectors in the displacement-vectors list whose y value satisfies $u_y - M_y/2 \leq y \leq u_y + M_y/2$. We shall term this set the y-window (in a sense it is a "window" on the full displacement-vectors list, defined by limiting y-values). Computationally, this set is simply all the displacement vectors whose address (in the displacement-vectors list) satisfies $\hat{Y}_{low} \leq \text{address} \leq \hat{Y}_{high}$.

We shall use the term "y-run" for the set of all displacement-vectors with the y-value. These displacement vectors are arranged consecutively in the displacement-vectors list and are ordered by increasing x-values. For each distinct y in the y-window, we keep a pair of pointers, $\hat{X}(y)_{low}$ and $\hat{X}(y)_{high}$. During a u-loop phase when $u_y$ stays constant, these pointer-pairs maintain the following conditions, similar to $\hat{Y}_{low}$ and $\hat{Y}_{high}$: $\hat{X}(y)_{low}$ points to an element in the y-run whose x value is the smallest and which satisfies $x \geq u_x - M_x/2$; and $\hat{X}(y)_{high}$ points to an element in the y-run whose x value is the smallest and which satisfies $x > u_x + M_x/2$. Whenever $u_y$ increases, we update $\hat{Y}_{low}$ and $\hat{Y}_{high}$ (box 46), and we reset all these pointer-pairs by pointing each pair to the beginning of its run (box 49). In each subsequent pass through the u-loop, when $u_x$ increases and $u_y$ does not change, all these pairs are incremented appropriately (in the same manner as $\hat{Y}_{low}$ and $\hat{Y}_{high}$ (box 47).

Now, all displacement vectors v contributing to W(u), which were defined to be those satisfying $|v_x - u_x| \leq M_x/2$, and $|v_y - u_y| \leq M_y/2$, are the union of sets corresponding to all y's in the y-window. Each such set consists of all displacement vectors whose address satisfies $\hat{X}(y)_{low} \leq \text{address} < \hat{X}(y)_{high}$. That is, W(u) is determined by counting all the displacement vectors (v) in the uncertainty box window using the $\hat{Y}_{low}$ and $\hat{Y}_{high}$ and the $\hat{X}(y)_{low}$ and the $\hat{X}(y)_{high}$ pointers (box 48).

Once W(u) is computed (box 44, FIG. 10), we find the best u, i.e., maximizing W(u) (box 50, FIG. 10). For this purpose, a vector v is found, for which $W(v) \geq W(u)$ for all u's. Then we determine (box 51) the vector w that maximizes W(t) among all vectors $t = (t_x, t_y)$ which lie outside the uncertainty-box centered around v, that is, which satisfy $$|t_x - v_x| > M_x/2 \text{ or } |t_y - v_y| > M_y/2 \qquad \text{Eq. 7}$$

Figure 14:
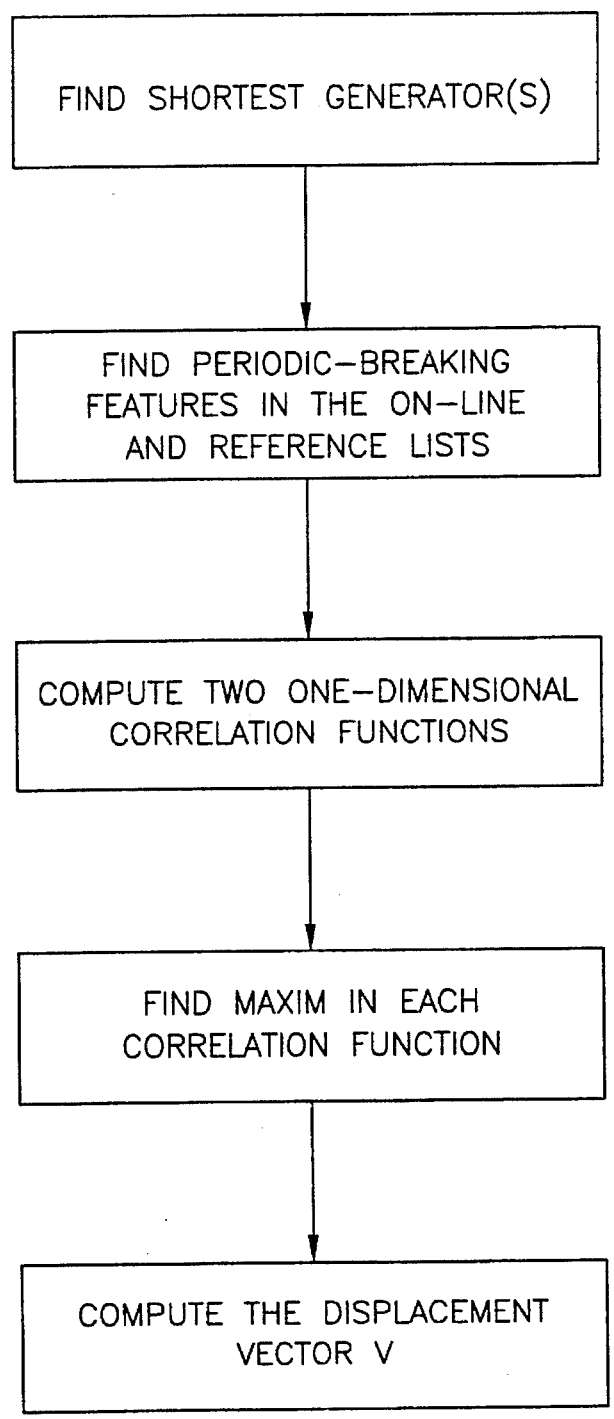
FIG. 14 is a flow chart illustrating an optional operation when periodic patterns are revealed in the inspected PCB.

It is helpful to think of v as the "most popular displacement vector", and of w as the "second most popular displacement vector". If $$\frac{W(v) - W(w)}{W(v) + W(w)} \leq 0.1$$

we deduce that the second most popular differs very little from the most popular vector, and so we suspect that the board is periodic (box 52) or has some other difficult structure; in such case we may revert to a special case algorithm (box 53) for computing w for periodic patterns. This special case is described below with reference to the flow chart illustrated in FIG. 14.

We can now estimate the translational part $\delta_x$, $\delta_y$ of the registration transformation parameters (box 54, FIG. 10). For this purpose we compute the 2-dimensional gaussian-weighted average, $\delta = (\delta x, \delta y)$, of all vectors t which satisfy $$|t_x - v_x| < M_x/2 \text{ and } |t_y - v_y| < M_y/2. \qquad \text{Eq. 8}$$

Returning to the boostrap flow chart of FIG. 8, after the translational parts ($\delta_x$, $\delta_y$) have been estimated (box 40, FIG. 8), the multiplicative parts (a, b, c, d) of the registration transformation parameters are now determined, and the translational parts are re-estimated (box 60), thus completing the bootstrap estimation of the misregistration parameters. To this end, we match each of the N online features (whose coordinates are indicated as $x_i$, $y_i$) against each reference feature with matching type and with coordinates (x', y'), such that $$|x' - (x_i + \delta_x)| < M_x/2 \text{ and } |y' - (y_i + \delta_y)| > M_y/2. \qquad \text{Eq. 9}$$

Note that an online feature may have more than one matching reference feature.

The memory area 13 (FIG. 6) of the slave processor includes eleven accumulating registers, named:

$$S, S_x, S_y, S_{x'}, S_{y'}, S_{xx'}, S_{yy'}, S_{xy'}, S_{yx'}$$

Figure 12:
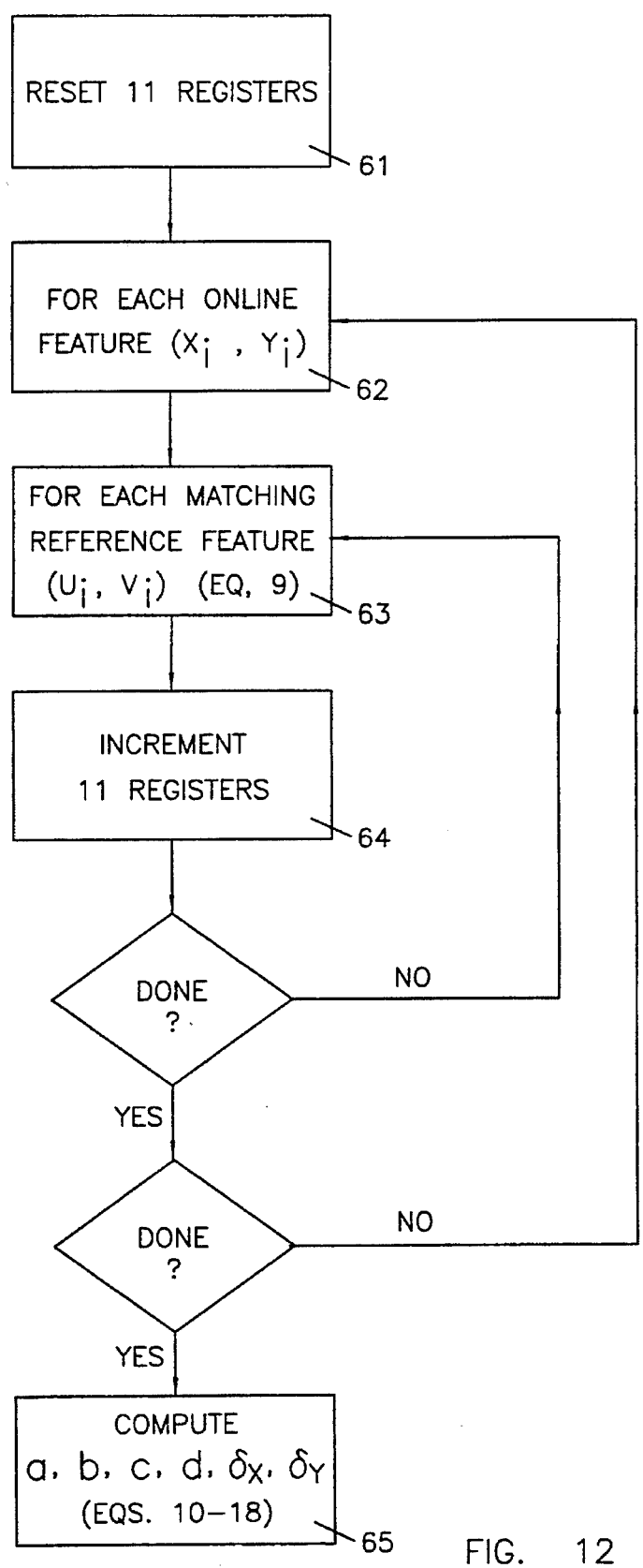

These registers are used in re-estimating the registration transformation parameters, as shown by the flow chart in FIG. 12.

Thus, according to the flow chart of FIG. 12 the eleven registers are reset (box 61). Each of the N online features (box 62) is paired with each of the matching reference features according to Equation 9 above, and the eleven registers are appropriately incremented (box 64).

Each of the above registers thus holds a sum to which a value is added for each matching pair. The registers are accumulated as follows: (x,y) and (x',y') denote a specific matching pair; the sums range over all matching pairs encountered up so far:

$$\begin{aligned} S &= \Sigma 1 \\ S_x &= \Sigma x \\ S_y &= \Sigma y \\ S_{x'} &= \Sigma x' \\ S_{y'} &= \Sigma y' \\ S_{xx'} &= \Sigma xx' \\ S_{yy'} &= \Sigma yy' \\ S_{xy'} &= \Sigma xy' \\ S_{yx'} &= \Sigma yx' \\ S_{xx} &= \Sigma x^2 \\ S_{yy} &= \Sigma y^2 \end{aligned} \qquad \text{Eq. 10}$$

A better approximation of the registration transformation parameters (for correcting article placement only) can now be computed (box 65) using the current values of the eleven registers, according to the following equations:

$$Wxx' = Sxx' - \frac{S_x S_{x'}}{S} \qquad \text{Eq. 11}$$

$$Wyy' = Syy' - \frac{S_y S_{y'}}{S} \qquad \text{Eq. 12}$$

$$Wxy' = Sxy' - \frac{S_x S_{y'}}{S} \qquad \text{Eq. 13}$$

$$Wyx' = Syx' - \frac{S_y S_{x'}}{S} \qquad \text{Eq. 14}$$

$$Wxx = Sxx - \frac{S_x^2}{S_2} \qquad \text{Eq. 15}$$

$$Wyy = Syy - \frac{S_y^2}{S} \qquad \text{Eq. 16}$$

-continued $$V = \sqrt{(W_{xx'} + W_{yy'})^2 + (W_{yx'} - W_{xy'})^2} \qquad \text{Eq. 17a}$$

$$\cos\theta = \frac{(W_{xx'} + W_{yy'})}{V} \qquad \text{Eq. 17b}$$

$$\sin\theta = \frac{(W_{yx'} - W_{xy'})}{V} \qquad \text{Eq. 17c}$$

$$\delta_x = \frac{S_{x'} - (S_x \cos\theta - S_y \sin\theta)}{S} \qquad \text{Eq. 17d}$$

$$\delta_y = \frac{S_{y'} - (+S_x \sin\theta + S_y \cos\theta)}{S} \qquad \text{Eq. 17e}$$

According to Eq. 1a: $a = \cos\theta$; $b = -\sin\theta$; $c = \sin\theta$; and $d = \cos\theta$ In the more general case, an estimation for the full affine transformation can be computed according to the following equations:

$$V = W_{xx} W_{yy} - W_{xy}^2 \qquad \text{FIG. 18a}$$

$$a = \frac{W_{yy} W_{xx'} - W_{xy} W_{yx'}}{V} \qquad \text{FIG. 18b}$$

$$b = \frac{W_{xx} W_{xy'} - W_{xy} W_{xx'}}{V} \qquad \text{FIG. 18c}$$

$$c = \frac{W_{yy} W_{yx'} - W_{xy} W_{yy'}}{V} \qquad \text{FIG. 18d}$$

$$d = \frac{W_{xx} W_{yy'} - W_{xy} W_{xy'}}{V} \qquad \text{FIG. 18e}$$

The above mathematical method of computing the registration transformation is based on the theory of least-squares data fitting, described, for example, in W. H. Press, B. P. Flannery, S. A. Teukolsky and W. T. Vetterling, Numerical Recipes, Cambridge University Press, 1986.

Our equations arise by applying the theory to the following problem: Given $(x_i, y_i)$ and $(x'_i, y'_i)$, $i = 1 \ldots n$, find $\delta x, \delta y$ and $a, b, c, d$ which minimizes the following expression:

$$\sum_i \left\| \begin{pmatrix} a & b \\ c & d \end{pmatrix} \begin{pmatrix} x_i \\ y_i \end{pmatrix} + \begin{pmatrix} \delta_x \\ \delta_y \end{pmatrix} - \begin{pmatrix} x'_i \\ y'_i \end{pmatrix} \right\|^2. \qquad \text{Eq. 19}$$

For article placement only, the minimization is constrained to rigid transformations.

The Main Procedure Following the completion of the bootstrap procedure (box 23, FIG. 7) for determining the registration transformation parameters on the initial scanned area, the system operates according to the main procedure. This consists of two processes working simultaneously, namely a comparison process and a fine-registration process, as indicated by box 24 in FIG. 7. The main procedure is more particularly illustrated in the flow chart of FIGS. 13 and 13b.

Figure 13A:
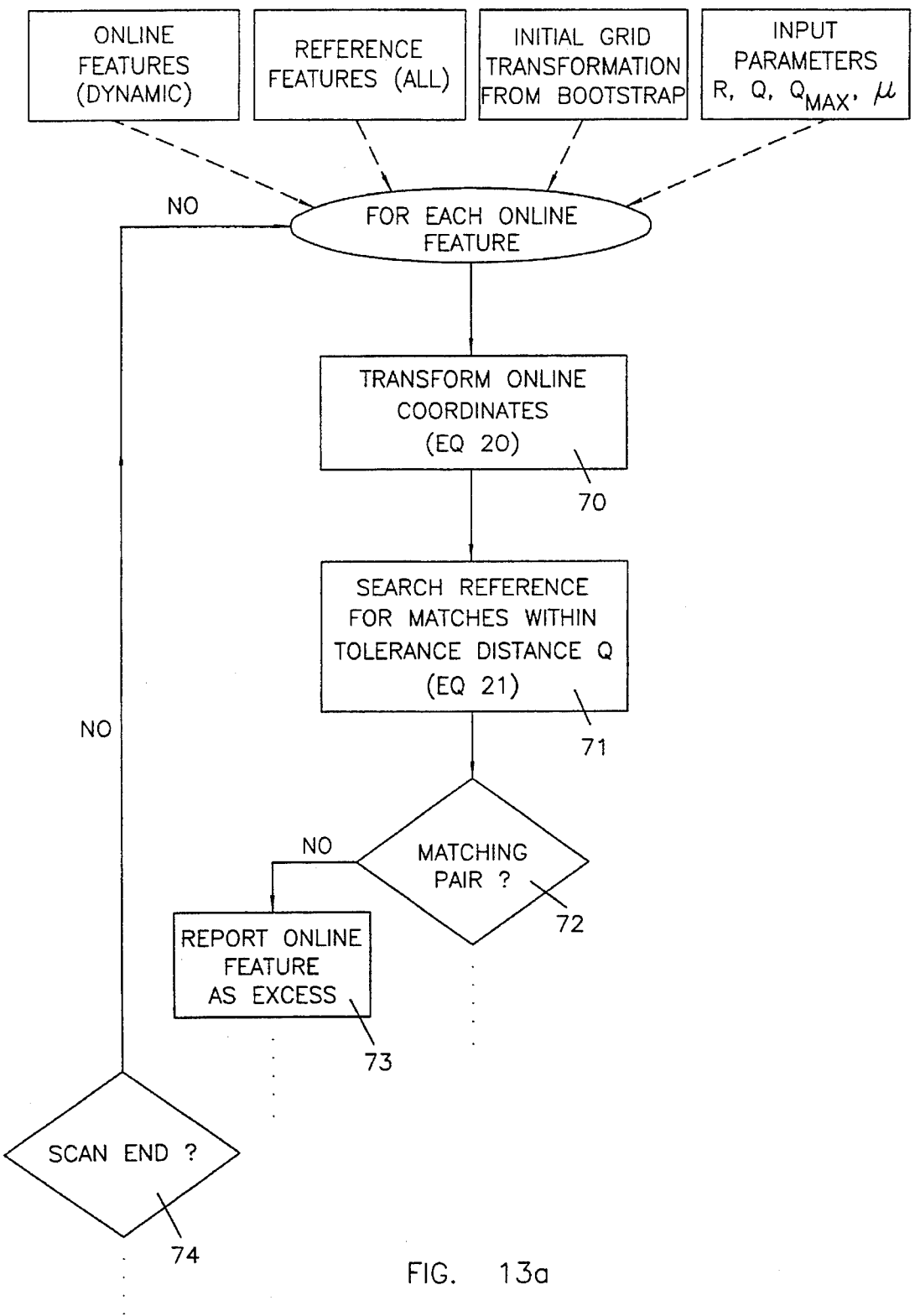
FIGS. 13a and 13b together constitute a flow chart illustrating the overall inspection process.
Figure 13B:
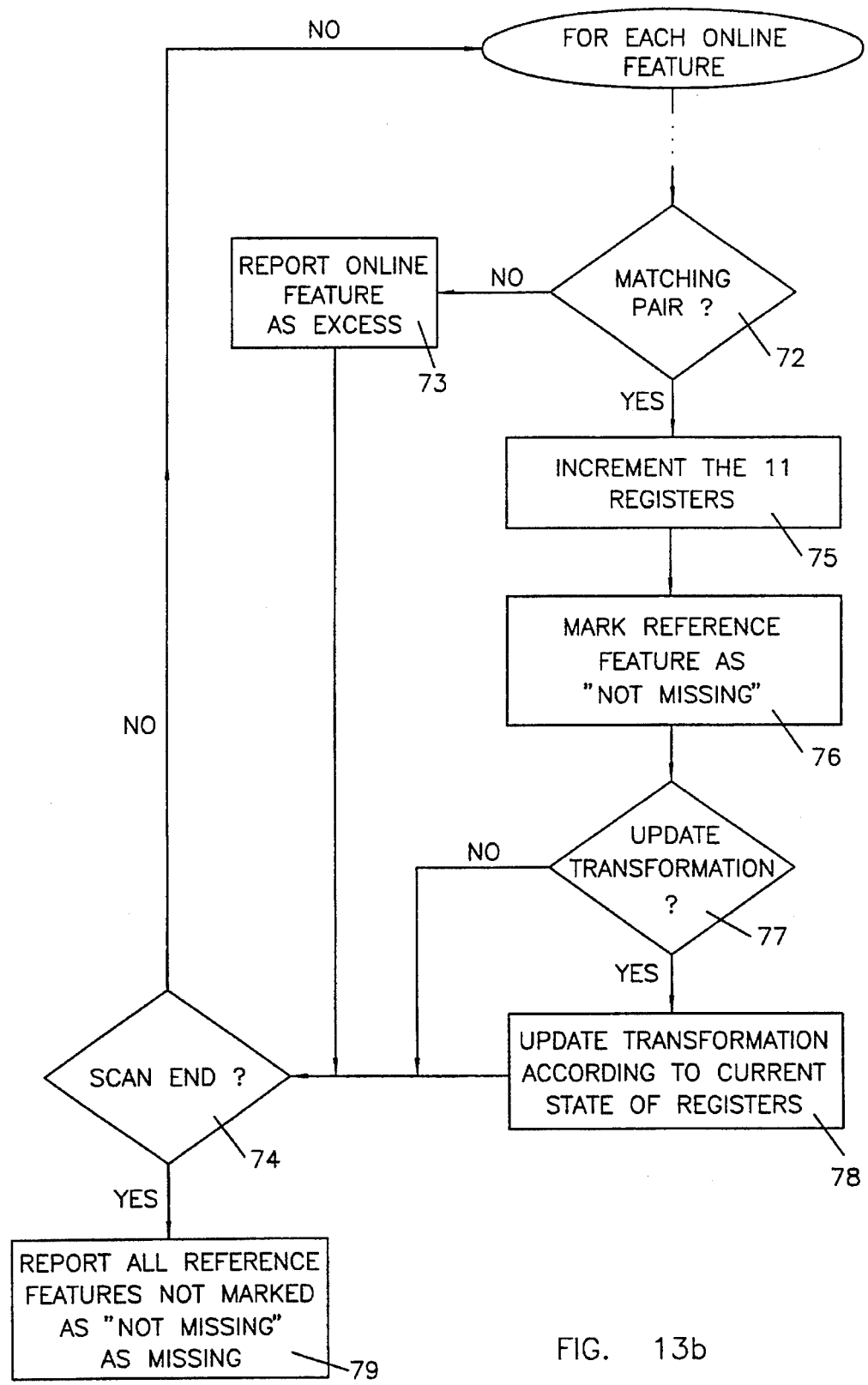

Thus, as indicated by box 70 in FIGS. 13a, 13b, when an online feature appears, with coordinates (x,y), its position is transformed, using the available transformation parameters, so as to be registered with the reference features, giving new coordinates (x',y') using Equation 1. Now, using these coordinates (x', y'), the reference list is searched for every feature with coordinates (x',y') that satisfy:

$$|x' - x^r| \leq Q \text{ and } |y' - y^r| \leq Q, \qquad \text{Eq. 20}$$

where Q is the reference tolerance, and of a type matching the online features type (box 71).

As indicated earlier, the transformation found in the booststrap procedure aligns the online features with the reference features in the initial scan zone. The bootstrap procedure operates on only a few online features, so that no time is lost waiting for a large number of online features to accumulate. The transformation produced by the bootstrap procedure may therefore not be the best transformation for the complete scanning zone. Fortunately, in the initial scan zone, better alignment is not yet required. However, as the scan continues over the complete scanning zone, a fine-registration process operates together with the main matching process in order to improve the transformation parameters.

Thus, as shown in the flow chart of FIGS. 13a, 13b, as each online feature is detected during the inspection process, it is compared with the stored reference features to see whether there are any matching pairs (box 72). If an online feature does not find a match with a stored reference feature, the online feature is recorded as an excess feature (box 73). On the other hand, if an online feature is matched with a stored reference feature (box 72), the eleven registers within the memory area 13 are updated (box 75) as described above, and the matching reference features are marked as "not missing" (box 76). This updating requires very little computation—only eleven additions and six multiplications.

Whenever it may be decided to update the transformation parameters (box 77), e.g., when enough online features have been collected or the scan has proceeded a large distance since the last update, this may be done (box 78) according to the current state of the eleven registers as in Equations 10-18.

At the end of the scan (box 74), all the reference features not marked as "not missing", are reported as "missing" (box 79). The system now reports a list of the excess features and missing features (box 25, FIG. 7).

The transformation parameters are also reported in order to facilitate high-level control or recording of the scanner geometrical distortion parameters derived from the transformation parameters.

It will thus be seen that, after the initial bootstrap procedure, the scan proceeds to provide more online features detected in the inspected PCB. This data may be used for updating the initial transformation parameters so as to increase their precision with the newly-arriving data. Athough the transformation parameters applied to the initially-scanned area are imprecise, they generally would be sufficient for the description of the transformation at the locale of the initially-scanned area so that it would not be necessary to return and rescan the initially-scanned area. Indeed, in principle the angle $\theta$, for example, cannot be measured accurately by using only a small zone. On the other hand, the exact angle is not necessary for accurate comparison of the initial zone to the reference. Only as the scan proceeds, a better approximation of the angle is needed, and is obtained with the arrival of more online data. Thus, the whole combined process of inspection and registration may be performed in a single scan.

When the scan of the first slice is finished, a good approximation of the first-slice transformation is achieved. However, as mentioned before, if scannner compensation is required, this transformation is only partially covered for the second slice. The parameters a, b, c, d are correct, but $\delta_x$ and $\delta_y$ for the second slice may differ slightly from those of the first. Thus, when scanner compensation is requested, the processing of the second-slice features is also preceded by a boot-strapping phase which uses the transformation from the previous slice. This bootstrap procedure operates with a much smaller search radius (R), assumes no angular discrepancy from the previous transformation ($\theta_{max} = 0$, $\alpha_{max} = 0$, $P_{Xmax} = 0$, $P_{Ymax} = 0$), and restricts itself to finding only translational deviations, thus changing only $\delta_x$ and $\delta_y$.

Optional Algorithm for Periodic Patterns

As mentioned above with respect to box 53 in the flow chart of FIG. 10, if a periodic board is found (box 52), a special algorithm for periodic patterns should be applied.

In the periodic case, the correlation function W( ) will have more than one significant peak. These peaks form geometrically a 2-dimensional grid. The first phase analyzes the correlation function W() to find the shortest grid generators. Generators of a 2-dimensional grid G are two linearly-independent vectors $g_1$ and $g_2$ so that all vectors in G can be obtained as a linear combination of $g_1$ and $g_2$ with coefficients $ng_1+mg_2$ where n, m belong to [. . . −2, −1, 0, 1, 2, 3, . . . ] (there may be only one generator if the periodicity is 1-dimensional). This is done by first applying a threshold to W( ) with the value of 80% of the highest value in W( ). Then the remaining displacement vectors are clusterized to form a 2-dimensional set of points $P_1$ - - - $P_m$ located at the cluster centers. Next, for each point in the set, $P_1$, the following is done:

1. The point in the set $P_1$ . . . $P_m$ which is closest to $P_1$ and is not $P_1$ itself is found. Call it $q_1$.
2. The subset of points that are not almost-collinear with $P_1$–$q_1$ is formed and from it the point closest to $P_1$ is found. We define "almost-collinear" as a third point V that makes the angle between V–$P_1$ and V–$q_1$—between +15° and −15° or between 180°+15° and 180°−15°. Call it $q_2$. The above subset may be empty, in which case $q_2$ is considered to be not found.
3. $q_1$–$P_1$ and $P_1$–$q_1$ are entered into a vector list called the "generator vector list". If $q_2$ was found $q_2$–$P_1$ and $P_1$–$q_2$ are entered into the list.

After going over all the points ($P_1$) and doing the above, the generator vector list is complete.

Now we take from this list the most abundant vector and name it $g_1$. Next, we search the list for the most abundant vector among those that are not almost in the direction of $g_1$ (again, in the 15° criterion). If there is no such vector, $g_1$ is the only generating vector. Otherwise, if we name it $g_2$ and $g_1$, $g_2$ are the two generating vectors.

Now that we have found the generators(s) we apply this knowledge to the feature-sets (online and reference) to find period-breaking features. In each of the two lists we do the following: for each feature having position f, we search in its own list for features in the proximity of positions $f+g_1$ and $f-g_1$, having a type that matches f's. If one (or both) of these positions has no matching features, and is inside the inspection zone (or slice boundaries, for the online list), f is marked as a period-breaker of type 1. The same is done for $g_2$ (searching positions $f+g_2$ and $f-g_2$ and marking as type 2), if $g_2$ indeed exists. We continue to process the list until enough period-breakers of type 1 are found and if $g_2$ exists, enough period-breakerts of type 2 are also found.

We define the following vectors:

$$U_1 = \begin{pmatrix} U_{1x} \\ U_{1y} \end{pmatrix} = \begin{pmatrix} -g_{2y} \\ g_{2x} \end{pmatrix}$$

$$U_2 = \begin{pmatrix} U_{2x} \\ U_{2y} \end{pmatrix} = \begin{pmatrix} -g_{1y} \\ g_{1x} \end{pmatrix}$$

otherwise, $$U_1 = \begin{pmatrix} g_{1x} \\ g_{1y} \end{pmatrix}$$

$$U_2 = \begin{pmatrix} -g_{1y} \\ g_{1x} \end{pmatrix}$$

And $$\hat{U}_1 = \frac{U_1}{\|U_1\|} = \frac{U_1}{\sqrt{U_{1x}^2 + U_{1y}^2}}$$

$$\hat{U}_2 = \frac{U_2}{\|U_2\|} = \frac{U_2}{\sqrt{U_{2x}^2 + U_{2y}^2}}$$

The vector $\hat{U}_1$ will serve as the direction in which a 1-dimensional correlation wil be computed between the online and reference period-breakers of type 1:

For each online feature which is a period-breaker of type 1 having coordinates (x, y) we search for all reference features within distance of R from (x, y), which are also period-breakers of type 1 and which have a type matching that of the online features. For each reference feature having coordinates ($x^1$, $y_1$) we compute:

$$Z=(x^1-x)U_{1x}+(y^1-y)U_{1y}$$

and increment the count for Z in the correlation fuction $C_1$( ), i.e., increment $C_1(Z)$, Z being the range $-\sqrt{2}R \ldots \sqrt{2}R$ (therefore $C_1$ is a vector in the range $-\sqrt{2}R \ldots \sqrt{2}R$). If $g_2$ exists we construct $C_2$( ) in the same way (looking for type 2 period breakers and using $U_{2x}$ and $U_{2y}$).

If $g_2$ does not exist we construct $C_2$( ) with type 1 period breakers, still using $U2_x$ and $U_{2y}$.

Now we find $Z_1$ so that $C_1(Z_1)$ is maximal in $C_1$( ), and $Z_2$ so that $C_2(Z_2)$ is maximal in $C_2$( ). From these compute the displacement vector V:

$$V_x=Z_1U_{1x}+Z_2U_{2x}$$

$$V_y=Z_1U_{1y}+Z_2U_{2y}$$

This V vector is the estimation of the correct displacement vector amongst the several that had high score in the original correlation function W( ). We continue with V as in the non-periodic case (see Eq. 8 and on and box 54 in FIG. 10).

Optional Registration Algorithm for Scanner Sensor Axis

As mentioned before, the scanner introduces distortions along the sensor axis. For a given slice and Y coordinates, this distortion is modeled along the scanner X axis—sensor axis as a polynomial of third degree. As the stage moves along the scanner Y axis this polynomial may change slowly. A third degree polynomial model is justified if we assume the distance between the light sensors and the article is a second degree polynomial as a function of X. Also lens magnification distortion as a function of X can be described as a second-degree polynomial. In a particular slice, the total of registration transformations becomes:

$$\begin{pmatrix} x \\ y \end{pmatrix} \to \begin{pmatrix} x+P_0(y)+P_1(y)x+P_2(y)x^2+P_3(y)x^3 \\ y \end{pmatrix} =$$

$$\begin{pmatrix} x^1 \\ y \end{pmatrix} \to \begin{pmatrix} ax^1+by+\delta x \\ cx^1+dy+\delta y \end{pmatrix} \to \begin{pmatrix} x^r \\ y^r \end{pmatrix}$$

where, x, y are scanned feature coordinates, $x^r$, $y^r$—reference (registered) coordinates. The algorithm for obtaining these extra model parameters $P_0(y)$, $P1(y)$, $P_2(y)$, $P_3(y)$ will be described.

Let us assume for the moment that a, b, c, d, and $\delta_x$, $\delta_y$ are already known. Denote by $a^1$, $b^1$, $c^1$, $d^1$, $\delta_x^1$, $\delta_y^1$ the parameters representing the inverse affine transformation (reference to online):

$$a^1 = \frac{d}{ad-bc}$$

$$b^1 = \frac{-b}{ad-bc}$$

$$c^1 = \frac{-c}{ad-bc}$$

$$d^1 = \frac{a}{ad-bc}$$

If $(x_i, y_i) \leftrightarrow (u_i, v_i)$ are the reference-online matches, we wish to model the error remaining after said transformation $(a^1 u_i + b^1 v_i + \delta^1 x) - x_i$ as a third-degree polynomial in $x_i$. We do this by least-squares fitting so we need the following:

$$S_x^k = \Sigma[X_i^k], (0 \leq k < 6)$$

$$\Sigma[x_i^k(a_i U_i + b^1 v_i + \delta x^1)] = (0 \leq k \leq 3)$$

$$= a^1 \Sigma[X_i^k U_i] + b_i \Sigma[X_i^k V_i] + \delta_x^1 \Sigma x_i^k =$$

$$= a^1 S_x^k u + b^1 S_x^k v + \delta x^1{}_s x^k$$

And then we solve the 4 by 4 linear system:

$$E_p = F \text{ for unknowns } P = \begin{matrix} P_0 \\ P_1 \\ P_2 \\ P_3 \end{matrix}$$

$$F_k = a^l S_x^k u + b^l S_x^k v + \delta_x^l S_x^k,$$

$$0 < k < 3$$

where $$E_{ml} = S_x^{m+l}$$

$$0 \leq m \leq 3$$
$$0 \leq l \leq 3$$

This is the procedure for obtaining the third degree polynomial coefficients $P_0$, $P_1$, $P_2$, $P_3$ given the match data $(X_i\ Y_i\ U_i\ V_i)$ and the affine transformation $(a, b, c, d\ \delta_x, \delta_y)$.

As can be seen, the information extracted from the matching data is independent of the affine transformation and can be gathered in fifteen accumulation registers:

$$S_X^{(n)}k = \sum_{l=1}^{n} x_l^k \qquad 0 =< k <= 6$$

$$S_X^{(n)}k_u = \sum_{l=1}^{n} x_l^k u_l \qquad 0 =< k <= 3$$

$$S_X^{(n)}k_v = \sum_{l=1}^{n} x_l^k v_l \qquad 0 =< k <= 3$$

where n is the number of the current match in this slice.

It was mentioned before that the polynomial may change Slowly with y during the slice scan. We incorporate this by making the registers accumulate match data with exponentially-decreasing weight for matches further back in Y:

$$S_X^{(n)}k = \sum_{l=1}^{n} q^{(yn-yl)} x_l^k \qquad 0 =< k <= 6$$

$$S_X^{(n)}k_u = \sum_{l=1}^{n} q^{(yn-yl)} x_l^k u_i \qquad 0 =< k <= 3$$

$$S_X^{(n)}k_v = \sum_{l=1}^{n} q^{(yn-yl)} x_l^k v_i \qquad 0 =< k <= 3$$

where OLqL1, q characterizes the special frequency of the changes in the distance between the sensors and this article.

This can also be accomplished in accumulators by:

$$S_x^{(n)}k = q^{(yn-yn-1)} S_X^{(n-1)}k + x_n^k \qquad 0 =< k <= 8$$

$$S_x^{(n)}k_u = q^{(yn-yn-1)} S_X^{(n-1)}k_u + x_n^k u_n \qquad 0 =< k <= 3$$

$$S_x^{(n)}k_v = q^{(yn-yn-1)} S_X^{(n-1)}k_v + x_n^k v_n \qquad 0 =< k <= 3$$

All this match-data accumulator-gathering process for the polynomial is merged in with the matching and lo gathering formulas for the affine transformation at the end of the bootstrap and during the scan. During the scan, as each match is found, it is used to update the eleven "affine" registers and the fifteen "polynomial" registers.

Periodically, the affine transformation is re-estimated using "affine" registers and the polynomial is re-estimated using the "polynomial" registers and the current affine transformation by solving the above 4×4 linear system.

While the invention has been described with respect to one preferred embodiment relating to compensation for rigid motion only, it will be appreciated that the novel method could also be used for compensating for any other type of misalignment, including parallel shift of the X-axis or Y-axis, or both; rotations full rigid motions scale error along the X-axis or Y-axis or both; perpendicularity error between the X-axis and Y-axis; and/or full linear distortion, generally expressed by the following equation with unknown parameters:

$$x'=ax+by+c$$

$$y'=dx+cy+f$$

Many other variations, modifications and applications of the invention may be made.

What is claimed is:

1. A method of inspecting an article with respect to a list of reference features each identified by its coordinate location, comprising:

scanning the article to generate online data, identifying detected features and their coordinates detected during the scanning of the article;

transforming the coordinates of the detected features according to registration transformation parameters to correct for global misregistration of the article;

and comparing the transformed coordinates of the detected features with those of the reference features for matches;

said registration transformation parameters of the overall article being determined by:

scanning an initial area of the article;

generating for said initial area, a list of said detected features with their coordinates;

pairwise matching said detected features and their coordinates with said reference features and their coordinates for said initial area;

computing an initial estimate of optimal registration transformation parameters required to minimize disparities between said pairwise matched detected and reference features in said initial area according to a misregistration transformation model;

and dynamically improving said initial estimate of the optimal transformation parameters by progressively increasing the scanned area of said article and progressively updating said initial estimate of the optimal transformation parameters according to said misregistration transformation model to provide optimal registration for the detected and reference features with respect to the complete area scanned.

2. The method according to claim 1, wherein computing said initial estimate of the optimal registration transformation parameters includes:

determining, for each detected feature in said initial area, all the reference features of the same type and within a maximal misregistration distance from the detected feature;

identifying such detected features and reference features as matching pairs;

and utilizing said matching pairs for computing said initial estimate of the optimal registration transformation parameters.

3. The method according to claim 2, wherein said matching pairs are utilized for computing said initial estimate of the optimal registration transformation parameters by:

determining, for each such matching pair, the displacement vector of the respective pair;

collecting all the displacement vectors for said initial area;

computing therefrom a correlation function;

and utilizing said correlation function for computing the initial estimate of the registration transformation parameters.

4. The method according to claim 3, wherein computing said correlation function includes:

defining a bounding box of the features in the initially scanned area;

defining an uncertainty box of the initially scanned area to allow for noise therein;

and counting all the vectors in the uncertainty box centered around the respective vector in the displacement vectors list for computing the correlation function of the respective vector in the displacement vectors list.

5. The method according to claim 1, wherein said initial estimate of the optimal transformation parameters is progressively updated by:

providing a plurality of registers for accumulating the coordinates of the detected features and the reference features;

incrementing the registers for the respective coordinates for each matching pair;

and utilizing the current values of the registers for updating the optimal transformation parameters.

6. The method according to claim 1, wherein the method is used to compensate for misregistration of the article because of article placement errors, scanner errors, and/or production scaling errors.

7. The method according to claim 1, wherein said article is optically scanned and its features are optically detected.

8. The method according to claim 1, wherein said article is a printed circuit board.

9. The method according to claim 1, wherein there is produced, as a result of inspecting the article, a list of excess features present in the inspected article but not in the stored list of reference features, and a list of missing features present in the stored list of reference features but not in the inspected article.

10. A method of inspecting an article with respect to a list of reference features each identified by its coordinate location and feature type, comprising:

computing an initial estimate of optimal registration transformation parameters of the overall article by:

optically scanning an initial area of the article to generate online data identifying detected features and their coordinates detected during the scanning of the article;

computing a displacement vector list of disparities between the detected features relative to the corresponding reference features;

computing an initial estimate of optimal registration transformation parameters required, according to a misregistration transformation model, to correct for said disparities due to misregistration of the article;

and dynamically improving said initial estimate of the optimal registration transformation parameters by progressively increasing the scanned area of said article and progressively updating said initial estimate of the optimal transformation parameters according to said misregistration transformation model to provide optimal registration for the detected and reference features with respect to the complete area scanned.

11. The method according to claim 10, wherein computing said initial estimate of the optimal registration transformation parameters includes:

determining, for each detected feature in said initial area, all the reference features of the same type and within a maximal misregistration distance from the detected feature;

identifying such detected features and reference features as matching pairs;

and utilizing said matching pairs for computing said initial estimate of the optimal registration transformation parameters.

12. The method according to claim 10, wherein said initial estimate of the optimal transformation parameters is progressively updated by:

providing a plurality of registers for accumulating the coordinates of the detected features and the reference features;

incrementing the registers for the respective coordinates for each matching pair;

and utilizing the current values of the registers for updating the optimal transformation parameters.

13. The method according to claim 12, wherein said matching pairs are utilized for computing said initial estimate of the optimal registration transformation parameters by:

determining, for each such matching pair, the displacement vector of the respective pair;

collecting all the displacement vectors for said initial area;

computing therefrom a correlation function;

and utilizing said correlation function for computing the initial estimate of the registration transformation parameters.

14. The method according to claim 13, wherein computing said correlation function includes:

defining a bounding box of the features in the initially scanned area;

defining an uncertainty box of the initially scanned area to allow for noise therein;

and counting all the vectors in the uncertainty box centered around the respective vector in the displacement vectors list for computing the correlation function of the respective vector in the displacement vectors list.

15. The method according to claim 10, wherein there is produced, as a result of inspecting the article, a list of excess features present in the inspected article but not in the stored list of reference features, and a list of missing features present in the stored list of reference features but not in the inspected article.

16. The method according to claim 10, wherein said article is a printed circuit board.

* * * * *